United States Patent

Nickias et al.

[11] Patent Number: 5,866,704
[45] Date of Patent: *Feb. 2, 1999

[54] 3-ARYL SUBSTITUTED INDENYL CONTAINING METAL COMPLEXES AND POLYMERIZATION PROCESS

[75] Inventors: Peter N. Nickias; Jasson T. Patton, both of Midland, Mich.

[73] Assignee: The Dow Chemical Company, Midland, Mich.

[ * ] Notice: The term of this patent shall not extend beyond the expiration date of Pat. No. 5,688,880.

[21] Appl. No.: 953,258

[22] Filed: Oct. 17, 1997

Related U.S. Application Data

[60] Provisional application No. 60/034,819 Dec. 19, 1996.
[51] Int. Cl.$^6$ .................. C07F 17/00; C07F 7/28
[52] U.S. Cl. .................. 556/11; 556/13; 556/19; 556/20; 556/53; 556/52; 502/103; 502/117; 526/127; 526/130; 526/134; 526/160; 526/943
[58] Field of Search .................. 556/11, 13, 19, 556/20, 52, 53; 502/103, 117; 526/127, 130, 134, 160, 943

[56] References Cited

U.S. PATENT DOCUMENTS 5,688,880 11/1997 Spencer et al. .................. 526/127

FOREIGN PATENT DOCUMENTS

| WO 95/00526 | 1/1995 | WIPO . |
| WO 95/14024 | 5/1995 | WIPO . |
| WO 96/07681 | 3/1996 | WIPO . |
| 97 15583 | 5/1997 | WIPO . |

*Primary Examiner*—Porfirio Nazario-Gonzalez

[57] ABSTRACT

Group 4 metal constrained geometry complexes comprising a 3-aryl- substituted indenyl ligand, catalytic derivatives thereof and their use as olefin polymerization catalysts, especially for preparing interpolymers comprising ethylene and a monovinyl aromatic monomer are disclosed.

3 Claims, No Drawings

3-ARYL SUBSTITUTED INDENYL CONTAINING METAL COMPLEXES AND POLYMERIZATION PROCESS

CROSS-REFERENCE STATEMENT

This application claims the benefit of U.S. Provisional Application Ser. No. 60/034,819 filed Dec. 19, 1996.

FIELD OF THE INVENTION

This invention relates to a class of Group 4 metal complexes and to polymerization catalysts derived therefrom that are particularly suitable for use in a polymerization process for preparing homopolymers and copolymers of α-olefins, especially copolymers comprising a monovinyl aromatic monomer and ethylene.

BACKGROUND

Constrained geometry metal complexes and methods for their preparation are disclosed in U.S. application Ser. No. 545,403, filed Jul. 3, 1990 (EP-A-416,815). This publication also teaches the preparation of certain novel copolymers of ethylene and a hindered vinyl monomer, including monovinyl aromatic monomers, having a pseudo-random incorporation of the hindered vinyl monomer therein. Additional teachings of constrained geometry catalysts may be found in U.S. application Ser. No. 547,718, filed Jul. 3, 1990 (EP-A-468,651); U.S. application Ser. No. 702,475, filed May 20, 1991 (EP-A-514,828); U.S. application Ser. No. 876,268, filed May 1, 1992, (EP-A-520,732) and U.S. application Ser. No. 8,003, filed Jan. 21, 1993 (WO93/19104), as well as U.S. Pat. No. 5,055,438, U.S. Pat. No. 5,057,475, U.S. Pat. No. 5,096,867, U.S. Pat. No. 5,064,802, U.S. Pat. No. 5,132,380, U.S. Pat. No. 5,470,993, WO95-00526 and U.S. Provisional application Ser. No. 60-005913. Variously substituted indenyl containing metal complexes have been taught in U.S. Ser. No. 592,756, filed Jan. 26, 1996, as well as WO95/14024. The teachings of all of the foregoing patents or the corresponding U.S. patent applications are hereby incorporated by reference.

SUMMARY OF THE INVENTION

According to the present invention there are provided metal complexes corresponding to the formula (I):

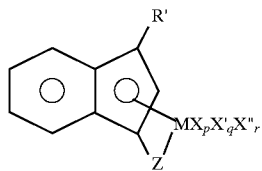

where M is titanium, zirconium or hafnium in the +2, +3 or +4 formal oxidation state;

R' is an aryl ligand or a halo-, silyl-, alkyl-, cycloalkyl-, dihydrocarbylamino-, hydrocarbyloxy-, or hydrocarbyleneamino-, substituted derivative thereof, said R' having from 6 to 40 nonhydrogen atoms;

Z is a divalent moiety, or a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic, delocalized, π-bound ligand groups;

X' independently each occurrence is a neutral Lewis base ligating compound having up to 20 atoms;

X" is a divalent anionic ligand group having up to 60 atoms;

p is zero, 1, 2, or 3;

q is zero, 1 or 2, and r is zero or 1.

The above complexes may exist as isolated crystals optionally in pure form or as a mixture with other complexes, in the form of a solvated adduct, optionally in a solvent, especially an organic liquid, as well as in the form of a dimer or chelated derivative thereof, wherein the chelating agent is an organic material such as ethylenediaminetetraacetic acid (EDTA).

Also, according to the present invention, there is provided a catalyst for olefin polymerization comprising:

A.
1) a metal complex of formula (I), and
2) an activating cocatalyst,
the molar ratio of 1) to 2) being from 1:10,000 to 100:1, or B.
the reaction product formed by converting a metal complex of formula (I) to an active catalyst by use of an activating technique.

Further according to the present invention there is provided a process for the polymerization of olefins comprising contacting one or more $C_{2-20}$ α-olefins under polymerization conditions with a catalyst comprising:

A.
1) a metal complex of formula (I), and
2) an activating cocatalyst,
the molar ratio of 1) to 2) being from 1:10,000 to 100:1, or B.
the reaction product formed by converting a metal complex of formula (I) to an active catalyst by use of an activating technique.

Finally according to the present invention there is provided a process for the preparation of copolymers of a monovinyl aromatic monomer and ethylene comprising contacting a mixture comprising one or more monovinyl aromatic monomers and ethylene under polymerization conditions with a catalyst comprising:

A.
1) a metal complex of formula (I), and
2) an activating cocatalyst,
the molar ratio of 1) to 2) being from 1:10,000 to 100:1, or B.
the reaction product formed by converting a metal complex of formula (I) to an active catalyst by use of an activating technique.

Use of the present catalysts and processes results in the highly efficient production of high molecular weight olefin polymers over a wide range of polymerization conditions, and especially at elevated temperatures. They are especially useful for the formation of copolymers of ethylene and styrene (ES polymers) and ethylene/styrene/diene (ESDM polymers) wherein the diene is ethylidenenorbornene, 1,4-hexadiene or similar nonconjugated diene. The use of the present novel polymerization catalysts allows for the incorporation of greater amounts of comonomer, especially vinyl aromatic comonomer into the copolymer per unit of catalyst due to combination of high catalyst efficiencies and high comonomer incorporation.

The catalysts of this invention may also be supported on a support material and used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

DETAILED DESCRIPTION

All reference to the Periodic Table of the Elements herein shall refer to the Periodic Table of the Elements, published and copyrighted by CRC Press, Inc., 1995. Also, any reference to a Group or Groups shall be to the Group or Groups as reflected in this Periodic Table of the Elements using the IUPAC system for numbering groups.

Olefins as used herein are $C_{2-100,000}$ aliphatic or aromatic compounds containing vinylic unsaturation, as well as cyclic compounds such as cyclobutene, cyclopentene, and norbornene, including norbornene substituted in the 5 and 6 position with $C_{1-20}$ hydrocarbyl groups. Also included are mixtures of such olefins as well as mixtures of such olefins with $C_{4-40}$ diolefin compounds. Examples of the latter compounds include ethylidene norbornene, 1,4-hexadiene, and norbornadiene. Long chain vinyl terminated monomers may be formed during the polymerization process, for example by the phenomenon of β-hydride elimination of a proton from a growing polymer chain. This process results in incorporation of extremely long chains into the resulting polymer, i. e. long chain branching. The catalysts and processes herein are especially suited for use in preparation of ethylene/1-butene, ethylene/1-hexene, ethylene/styrene, and ethylene/1-octene copolymers as well as terpolymers of ethylene, propylene and a nonconjugated diene, referred to as EPDM polymers, ethylene, styrene and a nonconjugated diene, referred to as ESDM polymers, or ethylene, propylene and styrene, referred to as EPS. Most preferred the catalysts and processes herein are used for the preparation of ethylene/styrene copolymers.

Monovinyl aromatic monomers for use herein include $C_{8-20}$ aryl substituted ethylene compounds having the formula:

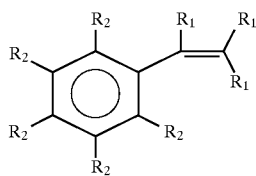

wherein:

$R_1$ independently each occurrence is hydrogen or $C_{1-4}$ alkyl, and $R_2$ independently each occurrence is $R_1$ or halo.

In the metal complexes, preferred X' groups are carbon monoxide; phosphines, especially trimethylphosphine, triethylphosphine, triphenylphosphine and bis(1,2-dimethylphosphino)ethane; $P(OR)_3$, wherein R is $C_{1-20}$ hydrocarbyl; ethers, especially tetrahydrofuran; amines, especially pyridine, bipyridine, tetramethylethylenediamine (TMEDA), and triethylamine; olefins; and conjugated dienes having from 4 to 40 carbon atoms. Complexes including diene X' groups include those wherein the metal is in the +2 formal oxidation state.

Further in reference to the metal complexes, X preferably is selected from the group consisting of halo, hydrocarbyl, and N,N-dialkylamino substituted hydrocarbyl. The number of X groups depends on the oxidation state of M, whether X is anionic, dianionic or neutral, whether Z is divalent or not and whether any divalent X" groups are present. The skilled artisan will appreciate that the quantity of the various substituents and the identity of Z are chosen to provide charge balance, thereby resulting in a neutral metal complex. For example, when Z is divalent, and r is zero, p is two less than the formal oxidation state of M. When Z contains one neutral two electron coordinate-covalent bonding site and M is in a formal oxidation state of +3, p may equal zero and r equal 1, or p may equal 2 and r equal zero. In a final example, if M is in a formal oxidation state of +2, Z may be a divalent ligand group, p and r may both equal zero and one neutral ligand group may be present.

Preferred coordination complexes used according to the present invention are complexes corresponding to the formula:

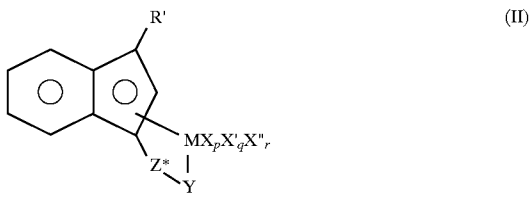

wherein:

R' is phenyl, biphenyl or naphthyl,

M is titanium;

Y is —O—, —S—, —NR*—, —PR*—; —NR$_2$*, or —PR$_2$*;

Z* is SiR*$_2$, CR*$_2$, SiR*$_2$SiR*$_2$, CR*$_2$CR*$_2$, CR*=CR*, CR*$_2$SiR*$_2$, or GeR*$_2$;

R* each occurrence is independently hydrogen, or a member selected from hydrocarbyl, hydrocarbyloxy, silyl, halogenated alkyl, halogenated aryl, and combinations thereof, said R* having up to 20 non-hydrogen atoms, and optionally, two R* groups from Z (when R* is not hydrogen), or an R* group from Z and an R* group from Y form a ring system;

X, X' and X" are as previously defined;

p is 0, 1 or 2;

q is zero or one; and r is zero or 1;

with the proviso that:

when p is 2, q and r are zero, M is in the +4 formal oxidation state (or M is in the +3 formal oxidation state if Y is —NR*$_2$ or —PR*$_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 nonhydrogen atoms, when r is 1, p and q are zero, M is in the +4 formal oxidation state, and X" is a dianionic ligand selected from the group consisting of hydrocarbadiyl, oxyhydrocarbyl, and hydrocarbylenedioxy groups, said X group having up to 30 nonhydrogen atoms, when p is 1, q and r are zero, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and when p and r are zero, q is 1, M is in the +2 formal oxidation state, and X' is a neutral, conjugated or nonconjugated diene, optionally substituted with one or more hydrocarbyl groups, said X' having up to 40 carbon atoms and forming a π-complex with M.

Most preferred metal complexes are those according to the previous formula (II) or (III), wherein M, X, X', X", R', Z*, Y, p, q and r are as previously defined, with the proviso that:

when p is 2, q and r are zero, M is in the +4 formal oxidation state, and X is independently each occurrence methyl, benzyl, or halide;

when p and q are zero, r is one, and M is in the +4 formal oxidation state, X" is a 1,4-butadienyl group that forms a metallocyclopentene ring with M, when p is 1, q and r are zero, M is in the +3 formal oxidation state, and X is 2-(N,N-dimethylamino)benzyl; and when p and r are 0, q is 1, M is in the +2 formal oxidation state, and X' is 1,4-diphenyl-1,3-butadiene or 1,3-pentadiene.

An especially preferred coordination complex is that corresponding to the formula:

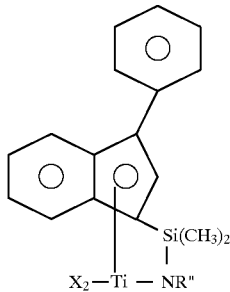

wherein R" is t-butyl and X is chloride, methyl or benzyl.

Illustrative metal complexes that may be employed in the practice of the present invention include:

3-Phenylindenyl Complexes
(t-butylamido)dimethyl($\eta^5$-3-phenylindenyl)silanetitanium (II) 1,4-diphenyl-1,3-butadiene,
(t-butylamido)dimethyl($\eta^5$-3-phenylindenyl)silanetitanium (II) 1,3-pentadiene,
(t-butylamido)dimethyl($\eta^5$-3-phenylindenyl)silanetitanium (III) 2-(N,N-dimethylamino)benzyl,
(t-butylamido)dimethyl($\eta^5$-3-phenylindenyl)silanetitanium (IV) dimethyl,
(t-butylamido)dimethyl($\eta^5$-3-phenylindenyl)silanetitanium (IV) dibenzyl,
(n-butylamido)dimethyl($\eta^5$-3-phenylindenyl)silanetitanium (II) 1,4-diphenyl-1,3-butadiene,
(n-butylamido)dimethyl($\eta^5$-3-phenylindenyl)silanetitanium (II) 1,3-pentadiene,
(n-butylamido)dimethyl($\eta^5$-3-phenylindenyl)silanetitanium (III) 2-(N,N-dimethylamino)benzyl,
(n-butylamido)dimethyl($\eta^5$-3-phenylindenyl)silanetitanium (IV) dimethyl,
(n-butylamido)dimethyl($\eta^5$-3-phenylindenyl)silanetitanium (IV) dibenzyl,
(cyclododecylamido)dimethyl($\eta^5$-3-phenylindenyl)silanetitanium(II) 1,4-diphenyl-1,3-butadiene,
(cyclododecylamido)dimethyl($\eta^5$-3-phenylindenyl)silanetitanium(II) 1,3-pentadiene,
(cyclododecylamido)dimethyl($\eta^5$-3-phenylindenyl)silanetitanium(III) 2-(N,N-dimethylamino)benzyl,
(cyclododecylamido)dimethyl($\eta^5$-3-phenylindenyl)silanetitanium(IV) dimethyl,
(cyclododecylamido)dimethyl($\eta^5$-3-phenylindenyl)silanetitanium(IV) dibenzyl,
(2,4,6-trimethylanilido)dimethyl($\eta^5$-3-phenylindenyl)silanetitanium(II) 1,4-diphenyl-1,3-butadiene,
(2,4,6-trimethylanilido)dimethyl($\eta^5$-3-phenylindenyl)silanetitanium(II) 1,3-pentadiene,
(2,4,6-trimethylanilido)dimethyl($\eta^5$-3-phenylindenyl)silanetitanium (III) 2-(N,N-dimethylamino)benzyl,
(2,4,6-trimethylanilido)dimethyl($\eta^5$-3-phenylindenyl)silanetitanium(IV) dimethyl,
(2,4,6-trimethylanilido)dimethyl($\eta^5$-3-phenylindenyl)silanetitanium(IV) dibenzyl,
(t-butylamido)dimethoxy($\eta^5$-3-phenylindenyl)silanetitanium (II) 1,4-diphenyl-1,3-butadiene,
(t-butylamido)dimethoxy($\eta^5$-3-phenylindenyl)silanetitanium(II) 1,3-pentadiene,
(t-butylamido)dimethoxy($\eta^5$-3-phenylindenyl)silanetitanium(III) 2-(N,N-dimethylamino)benzyl,
(t-butylamido)dimethoxy($\eta^5$-3-phenylindenyl)silanetitanium(IV) dimethyl,
(t-butylamido)dimethoxy($\eta^5$-3-phenylindenyl)silanetitanium(IV) dibenzyl, 3-Naphthylindenyl Complexes
(t-butylamido)dimethyl($\eta^5$-3-naphthylindenyl)silanetitanium (II) 1,4-diphenyl-1,3-butadiene,
(t-butylamido)dimethyl($\eta^5$-3-naphthylindenyl)silanetitanium (II) 1,3-pentadiene,
(t-butylamido)dimethyl($\eta^5$-3-naphthylindenyl)silanetitanium (III) 2-(N,N-dimethylamino)benzyl,
(t-butylamido)dimethyl($\eta^5$-3-naphthylindenyl)silanetitanium (IV) dimethyl, and
(t-butylamido)dimethyl($\eta^5$-3-naphthylindenyl)silanetitanium (IV) dibenzyl, 3-Biphenylindenyl Complexes
(t-butylamido)dimethyl($\eta^5$-3-biphenylindenyl)silanetitanium (II) 1,4-diphenyl-1,3-butadiene,
(t-butylamido)dimethyl($\eta^5$-3-biphenylindenyl)silanetitanium (II) 1,3-pentadiene,
(t-butylamido)dimethyl($\eta^5$-3-biphenylindenyl)silanetitanium (III) 2-(N,N-dimethylamino)benzyl,
(t-butylamido)dimethyl($\eta^5$-3-biphenylindenyl)silanetitanium (IV) dimethyl, and
(t-butylamido)dimethyl($\eta^5$-3-biphenylindenyl)silanetitanium (IV) dibenzyl.

The complexes can be prepared by use of well known synthetic techniques. Optionally a reducing agent can be employed to produce the lower oxidation state complexes. Such a process is disclosed in U.S. Ser. No. 08/241,523, filed May 13, 1994, published as WO95-00526, the teachings of which are hereby incorporated by reference. The reactions are conducted in a suitable noninterfering solvent at a temperature from −100° to 300° C., preferably from −78° to 100° C., most preferably from 0° to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, halocarbons, halohydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium- salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. 5,153,157, U.S. Pat. No. 5,064,802, EP-A-468,651 (equivalent to U.S. Ser. No. 07/547,718), EP-A-520,732 (equivalent to U.S. Ser. No. 07/876,268), and EP-A-520,732 (equivalent to U.S. Ser. Nos. 07/884,966 filed May 1, 1992), the teachings of which are hereby incorporated by reference.

Combinations of neutral Lewis acids, especially the combination of a trialkyl aluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluorophenylborane:alumoxane are from 1:1:1 to 1:5:20, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, A⁻. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

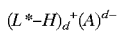

$(L^*-H)_d^+(A)^{d-}$ wherein:
L* is a neutral Lewis base;
(L*–H)+ is a Bronsted acid;
$A^{d-}$ is a noncoordinating, compatible anion having a charge of d–, and
d is an integer from 1 to 3.
More preferably $A^{d-}$ corresponds to the formula:

$[M'Q_4]^-$;

wherein:
M' is boron or aluminum in the +3 formal oxidation state; and
Q independently each occurrence is selected from hydride, dialkylamido, halide, hydrocarbyl, hydrocarbyloxide, halosubstituted-hydrocarbyl, halosubstituted hydrocarbyloxy, and halo- substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433, the teachings of which are herein incorporated by reference.

In a more preferred embodiment, d is one, that is, the counter ion has a single negative charge and is A⁻. Activating cocatalysts comprising boron which are particularly useful in the preparation of catalysts of this invention may be represented by the following general formula:

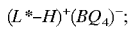

$(L^*-H)^+(BQ_4)^-$;

wherein:
L* is as previously defined;
B is boron in a formal oxidation state of 3; and
Q is a hydrocarbyl-, hydrocarbyloxy-, fluorinated hydrocarbyl-, fluorinated hydrocarbyloxy-, or fluorinated silylhydrocarbyl- group of up to 20 nonhydrogen atoms, with the proviso that in not more than one occasion is Q hydrocarbyl.

Preferred Lewis base salts are ammonium salts, more preferably trialkylammonium salts containing one or more $C_{12-40}$ alkyl groups. Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:
trimethylammonium tetrakis(pentafluorophenyl) borate,
triethylammonium tetrakis(pentafluorophenyl) borate,
tripropylammonium tetrakis(pentafluorophenyl) borate,
tri(n-butyl)ammonium tetrakis(pentafluorophenyl) borate,
tri(sec-butyl)ammonium tetrakis(pentafluorophenyl) borate,
N,N-dimethylanilinium tetrakis(pentafluorophenyl) borate, N,N-dimethylanilinium n-butyltris(pentafluorophenyl) borate,
N,N-dimethylanilinium benzyltris(pentafluorophenyl) borate,
N,N-dimethylanilinium tetrakis(4-(t-butyldimethylsilyl)-2, 3, 5, 6-tetrafluorophenyl) borate,
N,N-dimethylanilinium tetrakis(4-(triisopropylsilyl)-2, 3, 5, 6-tetrafluorophenyl) borate,
N,N-dimethylanilinium pentafluorophenoxytris (pentafluorophenyl) borate,
N,N-diethylanilinium tetrakis(pentafluorophenyl) borate,
N,N-dimethyl-2,4,6-trimethylanilinium tetrakis (pentafluorophenyl) borate,
dimethyloctadecylammonium tetrakis(pentafluorophenyl) borate,
methyldioctadecylammonium tetrakis(pentafluorophenyl) borate,
dialkyl ammonium salts such as:
di-(i-propyl)ammonium tetrakis(pentafluorophenyl) borate,
methyloctadecylammonium tetrakis(pentafluorophenyl) borate,
methyloctadodecylammonium tetrakis(pentafluorophenyl) borate, and
dioctadecylammonium tetrakis(pentafluorophenyl) borate;
tri-substituted phosphonium salts such as:
triphenylphosphonium tetrakis(pentafluorophenyl) borate,
methyldioctadecylphosphonium tetrakis(pentafluorophenyl) borate, and
tri(2,6-dimethylphenyl)phosphonium tetrakis (pentafluorophenyl) borate;
di-substituted oxonium salts such as:
diphenyloxonium tetrakis(pentafluorophenyl) borate,
di(o-tolyl)oxonium tetrakis(pentafluorophenyl) borate, and
di(octadecyl)oxonium tetrakis(pentafluorophenyl) borate;
di-substituted sulfonium salts such as:
di(o-tolyl)sulfonium tetrakis(pentafluorophenyl) borate, and
methylcotadecylsulfonium tetrakis(pentafluorophenyl) borate.

Preferred $(L^*\!-\!H)^+$ cations are methyldioctadecylammonium and dimethyloctadecylammonium.

Another suitable ion forming, activating cocatalyst comprises a salt of a cationic oxidizing agent and a noncoordinating, compatible anion represented by the formula:

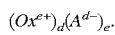

wherein:
$Ox^{e+}$ is a cationic oxidizing agent having a charge of e+;
e is an integer from 1 to 3; and
$A^{d-}$ and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion and a noncoordinating, compatible anion represented by the formula:

wherein:
$\copyright^+$ is a $C_{1-20}$ carbenium ion; and
$A^-$ is as previously defined. A preferred carbenium ion is the trityl cation, i.e. triphenylmethylium.

A further suitable ion forming, activating cocatalyst comprises a compound which is a salt of a silylium ion and a noncoordinating, compatible anion represented by the formula:

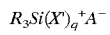

wherein:
R is $C_{1-10}$ hydrocarbyl, and X', q and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in J. Chem Soc. Chem. Comm., 1993, 383–384, as well as Lambert, J. B., et al., Organometallics, 1994, 13, 2430–2443. The use of the above silylium salts as activating cocatalysts for addition polymerization catalysts is disclosed in U.S. Ser. No. 304,314, filed Sep. 12, 1994, published in equivalent form as WO96/08519 on Mar. 21, 1996, the teachings of which are herein incorporated by reference.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433, the teachings of which are herein incorporated by reference.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0° to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, A−. Preferred supporting electrolytes are salts corresponding to the formula G$^+$A$^-$; wherein:

G$^+$ is a cation which is nonreactive towards the starting and resulting complex, and A$^-$ is as previously defined.

Examples of cations, G$^+$, include tetrahydrocarbyl substituted ammonium or phosphonium cations having up to 40 nonhydrogen atoms. Preferred cations are the tetra(n-butylammonium)- and tetraethylammonium- cations.

During activation of the complexes of the present invention by bulk electrolysis the cation of the supporting electrolyte passes to the counter electrode and A− migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl) borates having from 1 to 10 carbons in each hydrocarbyl or perfluoroaryl group, especially tetra (n-butylammonium)tetrakis(pentafluorophenyl) borate.

A further recently discovered electrochemical technique for generation of activating cocatalysts is the electrolysis of a disilane compound in the presence of a source of a noncoordinating compatible anion. This technique is more fully disclosed and claimed in the previously mentioned U.S. patent application Ser. No. 304,314.

The foregoing electrochemical activating technique and activating cocatalysts may also be used in combination. An especially preferred combination is a mixture of a tri (hydrocarbyl)aluminum or tri(hydrocarbyl)borane compound having from 1 to 4 carbons in each hydrocarbyl group with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris (pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The catalysts, whether or not supported in any of the foregoing methods, may be used to polymerize ethylenically and/or acetylenically unsaturated monomers having from 2 to 100,000 carbon atoms either alone or in combination. Preferred monomers include the $C_{2-20}$ α-olefins especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, tetrafluoroethylene, vinylbenzocyclobutane, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

Preferred monomers include a combination of ethylene and one or more comonomers selected from monovinyl aromatic monomers, 4-vinylcyclohexene, vinylcyclohexane, norbornadiene, ethylidene norbornene, $C_{3-10}$ aliphatic α-olefins (especially propylene, isobutylene, 1-butene, 1-hexene, 3-methyl-1-pentene, 4-methyl-1-pentene, and 1-octene), and $C_{4-40}$ dienes. Most preferred monomers are mixtures of ethylene and styrene; mixtures of ethylene, propylene and styrene; and mixtures of ethylene, styrene and a nonconjugated diene, especially ethylidenenorbornene.

In general, the polymerization may be accomplished at conditions well known in the prior art for Ziegler-Natta or Kaminsky-Sinn type polymerization reactions, that is, temperatures from 0°–250° C., preferably 30° to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}$:1 to $10^{-1}$:1, more preferably from $10^{-9}$:1 to $10^{-5}$:1.

Suitable solvents use for solution polymerization are inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770, as well as U.S. Ser. No. 08/10958, filed Jan. 29, 1993, the teachings or which are hereby incorporated by reference herein.

Utilizing the present catalysts, α-olefin homopolymers and copolymers having densities from 0.85 g/cm$^3$ to 0.96 g/cm$^3$, and melt flow rates from 0.001 to 10.0 dg/min are readily attained in a highly efficient process.

The catalysts of the present invention are particularly advantageous for the production of ethylene homopolymers and ethylene/α-olefin copolymers having high levels of long chain branching. The use of the catalysts of the present invention in continuous polymerization processes, especially continuous, solution polymerization processes, allows for elevated reactor temperatures which favor the formation of vinyl terminated polymer chains that may be incorporated into a growing polymer, thereby giving a long chain branch.

The use of the present catalysts system advantageously allows for the economical production of ethylene/α-olefin copolymers having processability similar to high pressure, free radical produced low density polyethylene.

The present catalysts system may be advantageously employed to prepare olefin polymers having improved processing properties by polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise ethylene, a $C_{3-20}$ α-olefin and a "H"-branching comonomer. Preferably, such polymers are produced in a solution process, most preferably a continuous solution process.

The catalyst composition may be prepared as a homogeneous catalyst by addition of the requisite components to a solvent in which polymerization will be carried out by solution polymerization procedures. The catalyst composition may also be prepared and employed as a heterogeneous catalyst by adsorbing the requisite components on an inert inorganic or organic particulated solid. Examples of such solids include, silica, silica gel, alumina, trialkylaluminum compounds, and organic or inorganic polymeric materials, especially polyolefins. In an preferred embodiment, a heterogeneous catalyst is prepared by co-precipitating the metal complex, an inert, inorganic compound and an activator, especially an ammonium salt of a hydroxyaryl (trispentafluorophenyl)borate, such as an ammonium salt of (4-hydroxy-3,5-ditertiarybutylphenyl) (trispentafluorophenylborate. A preferred inert, inorganic compound for use in this embodiment is a tri ($C_{1-4}$ alkyl) aluminum compound.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the α-olefin monomer or a mixture of different α-olefin monomers may be used in whole or part as the diluent. Most preferably, at least a major part of the diluent comprises the α-olefin monomer or monomers to be polymerized.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas such as, for example, nitrogen.

The polymerization may be carried out as a batchwise or a continuous polymerization process A continuous process is preferred, in which event catalyst, ethylene, comonomer, and optionally solvent are continuously supplied to the reaction zone and polymer product continuously removed therefrom.

Without limiting in any way the scope of the invention, one means for carrying out such a polymerization process is as follows: In a stirred-tank reactor, the monomers to be polymerized are introduced continuously together with solvent and an optional chain transfer agent. The reactor contains a liquid phase composed substantially of monomers together with any solvent or additional diluent and dissolved polymer. If desired, a small amount of a "H"-branch inducing diene such as norbornadiene, 1,7-octadiene or 1,9=decadiene may also be added. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mention chain transfer agent, such as a stream of hydrogen introduced to the reactor, as is well known in the art. The reactor effluent is contacted with a catalyst kill agent such as water. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from about 5 minutes to 8 hours, and preferably from 10 minutes to 6 hours. By using a catalyst that incorporates large amounts of hindered monovinyl monomer, hindered monovinyl homopolymer formed from residual quantities of the monomer are substantially reduced.

The process of the present invention can be employed to advantage in the gas phase copolymerization of olefins. Gas phase processes for the polymerization of olefins, especially the homopolymerization and copolymerization of ethylene and propylene, and the copolymerization of ethylene with higher α-olefins such as, for example, 1-butene, 1-hexene, 4-methyl-1-pentene are well known in the art. In such processes, cooling of the reactor may be provided by the use of recycle gas, which is fed as a volatile liquid to the bed to provide an evaporative cooling effect. The volatile liquid employed in this case can be, for example, a volatile inert liquid, for example, a saturated hydrocarbon having about 3 to about 8, preferably 4 to 6, carbon atoms. In the case that the monomer or comonomer itself is a volatile liquid (or can be condensed to provide such a liquid) this can be suitably fed to the bed to provide an evaporative cooling effect. Examples of olefin monomers which can be employed in this manner are olefins containing about three to about eight, preferably three to six carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream. This type of process is described, for example in EP 89691; U.S. Pat. No. 4,543,399; WO 94/25495 and U.S. Pat. No. 5,352,749, which are hereby incorporated by reference. A particularly preferred method of recycling the liquid to the bed is to separate the liquid from the recycle gas stream and to reinject this liquid directly into the bed, preferably using a method which generates fine droplets of the liquid within the bed. This type of process is described in BP Chemicals' WO 94/28032, which is hereby incorporated by reference.

The polymerization reaction occurring in the gas fluidized bed is catalyzed by the continuous or semi-continuous addition of catalyst. Such catalyst can be supported on an inorganic or organic support material as described above.

The polymer is produced directly in the fluidized bed by catalyzed copolymerization of the monomer and one or more comonomers on the fluidized particles of catalyst, supported catalyst or prepolymer within the bed. Start-up of the polymerization reaction is achieved using a bed of preformed polymer particles, which are preferably similar to the target polyolefin, and conditioning the bed according to techniques that are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a larger cross-sectional area than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization. The produced polymer is discharged continuously or discontinuously from the fluidized bed as desired.

The gas phase processes suitable for the practice of this invention are preferably continuous processes which provide for the continuous supply of reactants to the reaction zone of the reactor and the removal of products from the reaction zone of the reactor, thereby providing a steady-state environment on the macro scale in the reaction zone of the reactor.

Typically, the fluidized bed of the gas phase process is operated at temperatures greater than 50° C., preferably from about 60° C. to about 110° C., more preferably from about 70° C. to about 110° C.

Typically the molar ratio of comonomer to monomer used in the polymerization depends upon the desired density for the composition being produced and is about 0.5 or less. Desirably, when producing materials with a density range of from about 0.91 to about 0.93 the comonomer to monomer ratio is less than 0.2, preferably less than 0.05, even more preferably less than 0.02, and may even be less than 0.01. Typically, the ratio of hydrogen to monomer is less than about 0.5, preferably less than 0.2, more preferably less than 0.05, even more preferably less than 0.02 and may even be less than 0.01.

The above-described ranges of process variables are appropriate for the gas phase process of this invention and may be suitable for other processes adaptable to the practice of this invention.

A number of patents and patent applications describe gas phase processes which are adaptable for use in the process of this invention, particularly, U.S. Pat. Nos. 4,588,790; 4,543,399; 5,352,749; 5,436,304; 5,405,922; 5,462,999; 5,461,123; 5,453,471; 5,032,562; 5,028,670; 5,473,028; 5,106,804; 5,541,270 and EP applications 659,773; 692,500; and PCT Applications WO 94/29032, WO 94/25497, WO 94/25495, WO 94/28032; WO 95/13305; WO 94/26793; and WO 95/07942 the teachings of all of which are hereby incorporated herein by reference.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis.

$^1$H and $^{13}$C NMR spectra were recorded on a Varian XL (300 MHz) spectrometer. Tetrahydrofuran (THF), diethylether, toluene, and hexane were used following passage through double columns charged with activated alumina and copper/manganese mixed metal oxide catalyst (available from Engelhard Corp.). The compounds n-BuLi, all Grignard reagents, KH, indene, 1-indanone, and Ni(dppp)Cl$_2$ were all used as purchased from Aldrich. 2-Bromoindene, 2-methyl-4-phenylindene, and 2,4,6-trimethylindanone were all synthesized as described in literature. All syntheses were performed under dry nitrogen atmosphere using a combination of glove box and high vacuum techniques.

Example 1

Synthesis of: Dichloro[N-(t-butyl)-1,1-dimethyl-[3-phenylinden-1-yl]silanaminto(2-)-N]titanium (also referred to as dimethylsilyl(3-phenylindenyl)(t-butylamido)TiCl$_2$

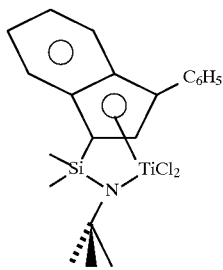

Preparation of 1-Phenylindene

1-Indanone (13.30 g, 0.1006 moles) was stirred in diethylether (300 mL) at −78° C. as PhMgBr (0.150 moles, 50.00 mL of 3.0M solution in diethylether) was added. The mixture was then allowed to slowly warm to 20°–25° C. and then stirred 16 hours. After the reaction period the mixture was poured on ice and then extracted with aqueous solutions of 1M HCl (1×100 mL), 1M NaHCO$_3$ (1×100 mL), and then H$_2$O (1×100 mL). The organic layer was then dried over MgSO$_4$. Filtration followed by removal of the volatiles resulted in the isolation of a yellow oil which by NMR was seen to still contain some 1-phenyl-1-indanol. This oil was then distilled under vacuum to yield the desired product as a pale yellow oil (18.56 g, 95.9 percent).

Preparation of Lithium-1-Phenylindenide

1-Phenylindene (6.00 g, 0.0312 moles) was stirred in hexane (300 mL) as nBuLi (0.0312 moles, 12.5 mL of 2.5M solution in hexane) was added dropwise. The mixture was then allowed to stir for 48 hours at 20°–25° C. during which time a solid precipitated. After the reaction period the solid was collected via suction filtration and was used without further purification or analysis (5.53 g, 89.4 percent).

Preparation of Dimethylsilyl(3-phenylindenyl)(t-butylamine)

Lithium-1-Phenylindenide (5.53 g, 0.0279 moles) in THF (50 mL) was added dropwise to a solution of dimethylsilyl (t-butylamino)chloride (4.62 g, 0.0279 moles) in THF (100 mL). This mixture was allowed to stir 16 hours. After the reaction period the volatiles were removed and the residue extracted and filtered using hexane. Removal of the hexane resulted in the isolation of the desired product as an oil (8.63 g, 96.2 percent).

Preparation of Dimethylsilyl(3-phenylindenyl)(t-butylamido)dilithide

Dimethylsilyl(3-phenylindenyl)(t-butylamine) (8.63 g, 0.0268 moles) was stirred in hexane (200 mL) as nBuLi (0.0537 moles, 21.5 mL of 2.5M solution in hexane) was added slowly. This mixture was then allowed to stir 16 hours during which time a sticky precipitate formed. The volatiles were then removed and the resulting yellow residue washed with hexane. After the reaction period the solid was dried and isolated as a yellow powder which was used without further purification or analysis (8.13 g, 91.0 percent).

Preparation of Dimethylsilyl(3-phenylindenyl)(t-butylamido)TiCl$_2$

Dimethylsilyl(3-phenylindenyl) (t-butylamsido)Li$_2$ (8.13 g, 0.0243 moles) was added slowly as a solid to a slurry of TiCl$_3$(THF)$_3$ (9.03 g, 0.0244 moles) in THF (30 mL). This mixture was allowed to stir for 30 minutes. PbCl$_2$ (3.38 g, 0.0122 moles) was then added as a solid and the mixture allowed to stir for an additional 45 minutes. After the reaction period the volatiles were removed and the residue extracted and filtered using toluene. Removal of the toluene resulted in the isolation of a dark residue which was then extracted with hexane and concentrated until solids precipitated. The precipitate was then collected via filtration and washed with cold hexane resulting in the isolation of a red-brown crystalline solid (7.39 g, 69.1 percent).

Example 2

Synthesis of: Dimethyl[N-(t-butyl)-1,1-dimethyl-[3-phenylinden-1-yl]silanaminto(2-)-N]titanium (also referred to as dimethylsilyl(3-phenylindenyl)(t-butylamido)TiMe$_2$ Dimethylsilyl(3-phenylindenyl)(t-butylamido)TiCl$_2$ (0.330 g, 0.000753 moles) was stirred in diethylether (30 mL) as MeMgI (0.00158 moles, 0.525 mL of 3.0M solution in diethylether) was added dropwise. This mixture was then allowed to stir for 40 minutes. After the reaction period the volatiles were removed and the residue extracted and filtered using hexane. Removal of the hexane resulted in the isolation of the desired product (0.210 g, 70.2 percent).

Example 3

Synthesis of: Dichloro[N-(cyclohexyl)-1,1-dimethyl-[3-phenylinden-1-yl]silanaminto(2-)-N] titanium (also referred to as dimethylsilyl(3-phenylindenyl)(cyclohexylamido)TiCl$_2$

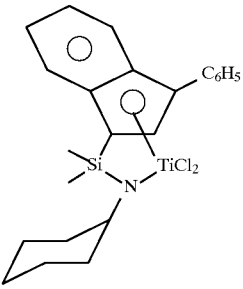

Preparation of Dimethylsilyl(3-phenylindenyl) chloride

Li-1-phenylindenide (21.8736 g, 0.1104 moles) in THF (75 mL) was added dropwise to a solution of Me$_2$SiCl$_2$ (51.3673 moles) in THF (150 mL). This mixture was then allowed to stir 16 hours. After the reaction period the volatiles were removed and the residue extracted and filtered using hexane. Removal of the hexane resulted in the isolation of the desired product as a yellow-red oil (28.6183 g, 91.0 percent).

Preparation of Dimethylsilyl(3-phenylindenyl) (cyclohexylamine)

Me$_2$Si(3-Phenylindenyl)Cl (4.7327 g, 0.01661 moles) was stirred in hexane (100 mL) as NEt$_3$ (5.1786 g, 0.05118 moles) and cyclohexylamine (1.6960 g, 0.01710 moles) were added. This mixture was then allowed to stir 16 hours. After the reaction period the mixture was filtered and the volatiles removed resulting in the isolation of the desired product as a yellow oil (5.2800 g, 91.7 percent).

Preparation of Dimethylsilyl(3-phenylindenyl) (cyclohexylamido)Li$_2$

Me$_2$Si(3-phenylindenyl)(cyclohexylamine) (5.2800 g, 0.001524 moles) was stirred in hexane (150 mL) as nBuLi (0.034 moles, 17.00 mL of 2.5M solution in hexane) was added slowly. This mixture was allowed to stir 16 hours during which time the mixture became a thick homogeneous oil. After the reaction period the volatiles were removed resulting in the isolation of a light yellow solid. This solid was then washed with hexanes and then dried resulting in the isolation of a light yellow powder which was used without further purification or analysis (4.4410 g, 81.3 percent).

Preparation of Dimethylsilyl(3-phenylindenyl) (cyclohexylamido)TiCl$_2$

Me$_2$Si(3-phenylindenyl) (cyclohexylamido)Li$_2$ (3.7346 g, 0.01042 moles) in THF (50 mL) was added dropwise to a slurry of TiCl$_3$(THF)$_3$ (3.8613 g, 0.01042 moles) in THF (100 mL). This mixture was allowed to stir for 2 hours. PbCl$_2$ (1.4513 g, 0.005219 moles) was then added as a solid and the mixture allowed to stir for an additional 45 minutes. After the reaction period the volatiles were removed and the residue extracted and filtered using toluene. Removal of the toluene resulted in the isolation of a dark residue which was then slurried in hexane and cooled to 0° C. The desired product was then collected via filtration as a red-brown crystalline solid (2.7475 g, 56.8 percent).

Example 4

Synthesis of: Dimethyl[N-(cyclohexyl)-1,1-dimethyl-[3-phenylinden-1-yl]silanaminto(2-)-N] titanium (also referred to as dimethylsilyl(3-phenylindenyl)(cyclohexylamido)TiMe$_2$ Me$_2$Si(3-phenylindenyl) (cyclohexylamido)TiCl$_2$ (0.3936 g, 0.0008476 moles) was stirred in diethylether (75 mL) as MeMgI (0.0017 moles, 0.57 mL of 3.0M solution in diethylether) was added dropwise. This mixture was then allowed to stir for 3 hours. After the reaction period the volatiles were removed and the residue extracted and filtered using hexane. Removal of the hexane resulted in the isolation of the desired product as a yellow-red residue (0.1404 g, 39.1 percent).

Polymerizations

The polymerization conditions are as follows: A two-liter Parr reactor is charged with approximately 360 g of Isopar-E™ mixed alkanes solvent (available from Exxon Chemicals Inc.) and about 460 g of styrene comonomer. Hydrogen is added as a molecular weight control agent by differential pressure expansion from a 75 mL addition tank at 25 psid (2070 kPa). The reactor is heated to 90° C. and saturated with ethylene at 200 psig (1.4 MPa) . The appropriate amount of catalyst and cocatalyst (trispentafluorophenylborane) as 0.005M solutions in toluene are premixed in the drybox to give a 1:1 molar ratio of catalyst and cocatalyst. After the desired premix time, the solution is transferred to a catalyst addition tank and injected into the reactor. The polymerization conditions are maintained for 30 minutes with ethylene on demand. Additional quantities of premixed catalyst are added periodically. The resulting solution is removed from the reactor, quenched with isopropyl alcohol and a hindered phenol antioxidant (Irganox™ 1010 from Ciba Geigy Corporation) is added to the resulting solution. Polymers formed are dried in a vacuum oven set at 135° C. for about 20 hours. Results using the catalysts of the invention and comparative catalyst, (indenyl)dimethyl(t-butylamido)silanetitanium dimethyl, are shown in Table 1.

TABLE 1

| complex | Efficiency[6] | styrene[7] | E × S[8] |
|---|---|---|---|
| pI[1] | 122,000 | 19.7 | 2.40 |
| I[2]* | 57,000 | 36.7 | 2.10 |
| MI[3] | 38,000 | 9.9 | 0.38 |
| TI[4]* | 20,000 | 37.1 | 0.74 |
| DI[5]* | 39,000 | 10.4 | 0.41 |

[1](N-t-butylamido)(dimethyl)(3-phenylindenyl)silanetitanium dimethyl;
[2](N-t-butylamido)(dimethyl)(indenyl)silanetitanium dimethyl;
*comparative, not an example of the invention
[6]grams polymer per gram Ti
[7]mole percent styrene
[8]Efficiency × percent styrene

What is claimed is:

1. A metal complex corresponding to the formula (I):

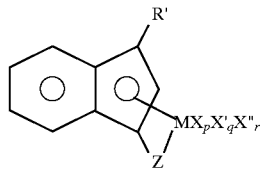

where M is titanium, zirconium or hafnium in the +2, +3 or +4 formal oxidation state;

R' is an aryl ligand or a halo-, silyl-, alkyl-, cycloalkyl-, dihydrocarbylamino-, hydrocarbyloxy-, or hydrocarbyleneamino-, substituted derivative thereof, said R' having from 6 to 40 nonhydrogen atoms;

Z is a divalent moiety, or a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic, delocalized, π-bound ligand groups;

X' independently each occurrence is a neutral Lewis base ligating compound having up to 20 atoms;

X" is a divalent anionic ligand group having up to 60 atoms;

p is zero, 1, 2, or 3;

q is zero, 1 or 2, and r is zero or 1.

2. The metal complex of claim 1 corresponding to the formula:

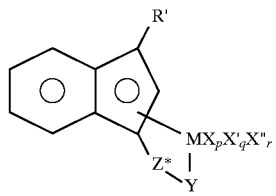

wherein:

R' is phenyl, biphenyl or naphthyl,

M is titanium;

Y is —O—, —S—, —NR*—, —PR*—; —NR$_2$*, or —PR$_2$*;

Z* is SiR*$_2$, CR*$_2$, SiR*$_2$SiR*$_2$, CR*$_2$CR*$_2$, CR*=CR*, CR*$_2$SiR*$_2$, or GeR*$_2$;

R* each occurrence is independently hydrogen, or a member selected from hydrocarbyl, hydrocarbyloxy, silyl, halogenated alkyl, halogenated aryl, and combinations thereof, said R* having up to 20 non-hydrogen atoms, and optionally, two R* groups from Z (when R* is not hydrogen), or an R* group from Z and an R* group from Y form a ring system;

X, X' and X" are as previously defined;

p is 0, 1 or 2;

q is zero or 1; and r is zero or 1;

with the proviso that:

when p is 2, q and r are zero, M is in the +4 formal oxidation state (or M is in the +3 formal oxidation state if Y is —NR*$_2$ or —PR*$_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 nonhydrogen atoms, when r is 1, p and q are zero, M is in the +4 formal oxidation state, and X" is a dianionic ligand selected from the group consisting of hydrocarbadiyl, oxyhydrocarbyl, and hydrocarbylenedioxy groups, said X group having up to 30 nonhydrogen atoms, when p is 1, q and r are zero, M is in the +3 formal oxidation state, and X is a stabilizing anionic ligand group selected from the group consisting of allyl, 2-(N,N-dimethylamino)phenyl, 2-(N,N-dimetihylaminomethyl)phenyl, and 2-(N,N-dimethylamino)benzyl, and when p and r are zero, q is 1, M is in the +2 formal oxidation state, and X' is a neutral, conjugated or nonconjugated diene, optionally substituted with one or more hydrocarbyl groups, said X' having up to 40 carbon atoms and forming a π-complex with M.

3. The metal complex of claim 2 which is (3-phenylindenyl)dimethyl(t-butylamido)silanetitanium dichloride, (3-phenylindenyl)dimethyl(t-butylamido)silanetitanium dimethyl, (3-phenylindenyl)dimethyl(cyclohexylamido)silanetitanium dichloride, or (3-phenylindenyl)dimethyl(cyclohexylamido)silanetitanium dimethyl.

* * * * *